United States Patent
Doric et al.

(10) Patent No.: US 9,791,683 B2
(45) Date of Patent: Oct. 17, 2017

(54) MICROSCOPE WITH MULTIPLE ILLUMINATION CHANNELS FOR OPTOGENETIC STIMULATION AND FLUORESCENCE IMAGING

(71) Applicant: Optomak, Inc., Quebec (CA)

(72) Inventors: Sead Doric, L'Ancienne-Lorette (CA); Harold Dehez, Quebec (CA); Olivier Dupont-Therrien, Quebec City (CA)

(73) Assignee: OPTOMAK, INC. (CA)

( * ) Notice: Subject to any disclaimer, the term of this patent is extended or adjusted under 35 U.S.C. 154(b) by 21 days.

(21) Appl. No.: 14/991,208

(22) Filed: Jan. 8, 2016

(65) Prior Publication Data
US 2017/0199364 A1     Jul. 13, 2017

(51) Int. Cl.
*G02B 21/06* (2006.01)
*A61B 5/00* (2006.01)
*A61N 5/06* (2006.01)
*G02B 21/08* (2006.01)
*G02B 13/00* (2006.01)
(Continued)

(52) U.S. Cl.
CPC .......... *G02B 21/082* (2013.01); *A61B 5/0071* (2013.01); *A61N 5/0622* (2013.01); *G02B 6/0006* (2013.01); *G02B 13/0095* (2013.01); *G02B 21/0008* (2013.01); *G02B 21/02* (2013.01); *G02B 21/16* (2013.01); *G02B 27/141* (2013.01)

(58) Field of Classification Search
CPC ................ G02B 21/082; G02B 6/0006; G02B 13/0095; G02B 21/0008; G02B 21/02; G02B 21/16; G02B 27/141; A61B 5/0071; A61N 5/0622

USPC ..... 359/363, 381, 385, 389, 390; 250/458.1, 250/459.1

See application file for complete search history.

(56) References Cited

U.S. PATENT DOCUMENTS 6,101,028 A     8/2000 Heacock et al.
6,508,759 B1 *  1/2003 Taylor ................ A61B 1/00149
                                                    359/381
(Continued)

FOREIGN PATENT DOCUMENTS

WO    WO 2016187715 A1    12/2016
WO    WO 2017079688 A1    5/2017

OTHER PUBLICATIONS

Helmchen et al, "A Miniature Head-Mounted Two-Photon Microscope: High-Resolution Brain Imaging in Freely Moving Animals," Neuron, vol. 31, 903-912, Sep. 27, 2001.*

(Continued)

*Primary Examiner* — Frank Font
(74) *Attorney, Agent, or Firm* — Mitch Harris, Atty at Law, LLC; Andrew M. Harris (57) ABSTRACT

A miniaturized microscope provides the combined capability for simultaneous or sequential optogenetic stimulation of light sensitive ion channels with the capability for fluorescence imaging of fluorescent proteins for applications requiring simultaneous optical stimulation and monitoring of cell activity. The microscope includes a dual illumination output coupling for providing illumination to two different regions within the sample and/or two different illumination source inputs and a dual transmission band optical filter to clean two different bands of light that are separately available for optogenetic stimulation and fluorescence imaging.

21 Claims, 12 Drawing Sheets

(51) Int. Cl.
*G02B 21/02* (2006.01)
*F21V 8/00* (2006.01)
*G02B 27/14* (2006.01)
*G02B 21/16* (2006.01)
*G02B 21/00* (2006.01)

(56) References Cited

U.S. PATENT DOCUMENTS

| | | | |
|---|---|---|---|
| 6,643,071 B2 | 11/2003 | Schnitzer | |
| 6,847,480 B2 | 1/2005 | Steenblik et al. | |
| 7,262,923 B2 * | 8/2007 | Quake | B01L 3/502715 359/368 |
| 8,346,346 B1 | 1/2013 | Schnitzer et al. | |
| 8,624,967 B2 | 1/2014 | O'Connell et al. | |
| 8,840,566 B2 * | 9/2014 | Seibel | A61B 1/0008 600/176 |
| 9,046,659 B2 | 6/2015 | Doric | |
| 9,195,043 B2 | 11/2015 | Ghosh et al. | |
| 9,207,405 B2 | 12/2015 | Doric | |
| 9,696,897 B2 * | 7/2017 | Garcia | G06F 3/0487 |
| 2003/0187427 A1 * | 10/2003 | Gatto | A61B 1/043 606/15 |
| 2010/0007947 A1 * | 1/2010 | Lembke | G02B 21/26 359/393 |
| 2011/0224554 A1 * | 9/2011 | Vukeljic | G02B 6/3882 600/478 |
| 2012/0016429 A1 * | 1/2012 | Klorg | A61N 5/0601 607/2 |
| 2014/0036364 A1 | 2/2014 | Doric | |
| 2014/0367590 A1 * | 12/2014 | Walla | G02B 21/0068 250/459.1 |
| 2015/0309295 A1 | 10/2015 | Cocker et al. | |
| 2015/0366437 A1 * | 12/2015 | Labrie | A61B 5/0084 600/373 |
| 2016/0131334 A1 * | 5/2016 | Rousseau | G02B 6/0006 362/19 |
| 2017/0059841 A1 | 3/2017 | Trulson et al. | |

OTHER PUBLICATIONS

Murakami et al., "A Miniature Confocal Optical Microscope With Mems Gimbal Scanner." the 12.sup.th International Conference on Solid State Sensors, Actuators and Microsystems Boston: 587-590, Jun. 8-12, 2003.*

Bergeron, Louis, Stanford Report, "Fingertip-size microscope has huge potential for studying the brain and its diseases, say Stanford researchers", Sep. 16, 2011, downloaded from http://news.stanford.edu/news/2011/september/fingertip-size-microscope-091611.html on Apr. 30, 2017.*

Ghosh et al., "Miniaturized integration of a fluorescence microscope", Nat Methods, vol. 8(10), pp. 871-878, Published online Sep. 11, 2011.*

El Gamal et al., "Two-gram microscopes make brain images in moving mice", Nature Methods, vol. 8 No. 10, Oct. 2011, pp. 781.*

Ghosh, et al., "Miniaturized integration of a fluorescence microscope", Nature Methods, Oct. 2011, pp. 871-882, vol. 8, No. 10, Nature Publishing Group, London.

Ziv, et al., "Long-term dynamics of CA1 hippocampal place codes", Nature Neuroscience, Feb. 2013, 5 pages (pp. 1-5 in pdf), 16(3).

Flusberg, et al., "High-speed, miniaturized fluorescence microscopy in freely moving mice", Nature Methods, Nov. 2008, pp. 935-938, vol. 5, No. 11, Nature Publishing Group, London.

U.S. Appl. No. 62/383,122 filed on Sep 2 2016, 132 pages (pp. 1-132 in pdf).

U.S. Appl. No. 62/251,501 filed on Nov. 5 2015, 70 pages (pp. 1-70 in pdf).

* cited by examiner

MICROSCOPE WITH MULTIPLE ILLUMINATION CHANNELS FOR OPTOGENETIC STIMULATION AND FLUORESCENCE IMAGING

BACKGROUND OF THE INVENTION

1. Field of the Invention

The present invention relates to biological microscopy, and more particularly concerns a microscope probe for in vivo or in vitro optogenetic stimulation and fluorescence imaging through multiple illumination channels.

2. Background of the Invention

When making microscopic observations of in vivo biological specimens, minimally invasive techniques are required. However, conventional microscopes feature large size microscope objectives. Large objectives cannot be implanted within a sample without causing significant damage to the sample, such as removing structures in order to facilitate access to deep layers within the sample. Less invasive fiber-optic cannulae that are typically used in optogenetics experiments are typically configured only for optical stimulation or silencing of a certain class of neurons without imaging capabilities. More recent solutions include miniaturized microscopes that can be detachably coupled to a base plate mounted on a subject, such as those disclosed in U.S. Patent Application Publications U.S. 20120062723 and U.S. 20150309295.

While the ability to perform fluorescence microscopy in in vivo and in vitro configurations is desirable, for optogenetic applications, existing systems are limited in their flexibility of performing optogenetic stimulation.

Therefore, it would be desirable to provide an optogenetic compatible fluorescence microscope.

SUMMARY OF THE INVENTION

The invention encompasses microscopes capable of performing optogenetic stimulation and fluorescence imaging on a sample having an attached optical cannula, which is a fixture on the sample having one or more optical probes focusing and/or extending into the sample for delivering light into and receiving light from regions or points within the sample. The invention also encompasses a method of performing optogenetic stimulation and fluorescence imaging on a sample. The optogenetic stimulation and fluorescence imaging can thus be synchronized so that simultaneous or sequential optogenetic stimulation and fluorescence imaging measurements are performed.

In one aspect, the microscope includes a first connector for receiving an optical illumination connection coupling light from two or more illumination sources and a second connector adapted to mechanically connect to the cannula. The second connector includes one or more optical interfaces for coupling light returning from the sample to the microscope and coupling illumination from the illumination sources to the sample. The microscope further includes an optical filter having a dual band-pass transmission spectrum characteristic for filtering the light provided by the illumination sources, so that the transmitting bands correspond to the wavelengths of the illumination sources.

In another aspect, the illumination connection couples light from one or more illumination sources, but to two different regions of the sample via the second connector having separate optical interfaces for coupling light from at least one illumination source to the different regions of the sample.

The foregoing and other objectives, features, and advantages of the invention will be apparent from the following, more particular, description of the preferred embodiment of the invention, as illustrated in the accompanying drawings.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein like reference numerals indicate like components, and:

DESCRIPTION OF ILLUSTRATED EMBODIMENT

The systems described herein are miniaturized multimodal systems of generally less than a cubic inch in size that combine capability for optical stimulation of light sensitive ion channels (optogenetic stimulation) with capability for fluorescence imaging of fluorescent proteins for applications requiring simultaneous or sequential optical stimulation and monitoring of cell activity. The system includes an objective lens to create a magnified image of a region of the sample on an image sensor. The objective lens may be integrated in a microscope or be integrated in a cannula to which the microscope is attached. The microscope generally includes one or more filters to separate illumination light from fluorescence signal and a connection for receiving illumination light from at least two external light sources with an optical arrangement to bring illumination lights to the subject: one source for fluorescence imaging and the other for optogenetic stimulation of the region of interest. Alternatively, or in combination, the cannula and connection to the cannula may include two different illumination paths to either perform fluorescence imaging in one region and optogenetic stimulation in another region or perform both fluorescence imaging in one region and optogenetic stimulation in each region. The miniaturized system is configured to easily connect to and disconnect from the cannula and includes a specific connector adapted to provide precise optical alignment with the cannula, which may be a cannula such as those described in U.S. patent application Ser. No. 14/310,012 entitled "IMAGE RELAYING CANNULA WITH DETACHABLE SELF-ALIGNING CONNECTOR" filed on Jun. 20, 2014, the disclosure of which is incorporated herein by reference. The imaging system is designed to observe a field or fields of view smaller than 0.5 mm$^2$ (to reduce invasiveness) with a spatial resolution at the micron scale.

Optogenetics experiments use light to control the activity of cells in living tissues, and of particular interest is the modulation of neuronal activity in the brain. To become light sensitive, the cells under study are marked with genetically encoded light sensitive ion channels (e.g., channelrhodopsine, halorhodopsine, etc.). Fluorescence imaging of functional fluorescent proteins (e.g., a genetically encoded calcium indicator) is an optical method used to monitor the activity of cells. The systems described herein are multimodal systems that can combine simultaneous or sequential optogenetics stimulation of light sensitive ion channels with fluorescence imaging of fluorescent proteins in a miniature package of less than a cubic inch in size for applications requiring simultaneous optical stimulation and monitoring of cell activity.

To prevent cross-talk between the different optical modalities in the multimodal optical system (e.g. combination of fluorescence imaging with optogenetic stimulation), the illumination light of each modality must be spectrally and/or spatially distinct. In the systems described herein, the excitation source is generally external and interchangeable so that two or more excitation lights, i.e., illumination sources, can be coupled to the system. The illumination sources are optically coupled to the miniature microscope via a connector. In configurations having a single implant in the sample with a corresponding single optical coupling between the cannula and the microscope, two light sources are used, one for fluorescence imaging and the second for optogenetic stimulation. An included optical filter set is specifically designed to bring the two bands of illumination light (for imaging and stimulation) to the sample and collect the fluorescence signal from the cannula and direct it to an image sensor. In another configuration, the modalities are spatially separated by providing two implants in the sample to target two specific areas, and providing corresponding optical couplings between the cannula and the microscope. The implants may be a relay lens, e.g. a GRIN lens, and/or a fiber optic. The relay lens may be implanted in one area for epi-fluorescence imaging and optogenetic stimulation, and a fiber optic may be implanted for optogenetic stimulation only. Other configurations and combinations such as those disclosed herein or otherwise provided by combining elements that are shown by the present disclosure or their equivalents are contemplated and the examples chosen as illustrations should not be considered limiting. In the examples given herein, the field of view of the microscope described herein is less than 0.5 mm$^2$ and having a spatial resolution at the micron scale, which also differs from existing miniature microscope systems. By limiting the field of view to less than 0.5 mm$^2$, the volume of the microscope can be reduced and the image quality improved over the field of view. To improve the portability and facilitate the access to a confined region of interest, the total size of the miniaturized microscope can be maintained below 1 in$^3$ with a weight of under 4 g.

Figure 1:
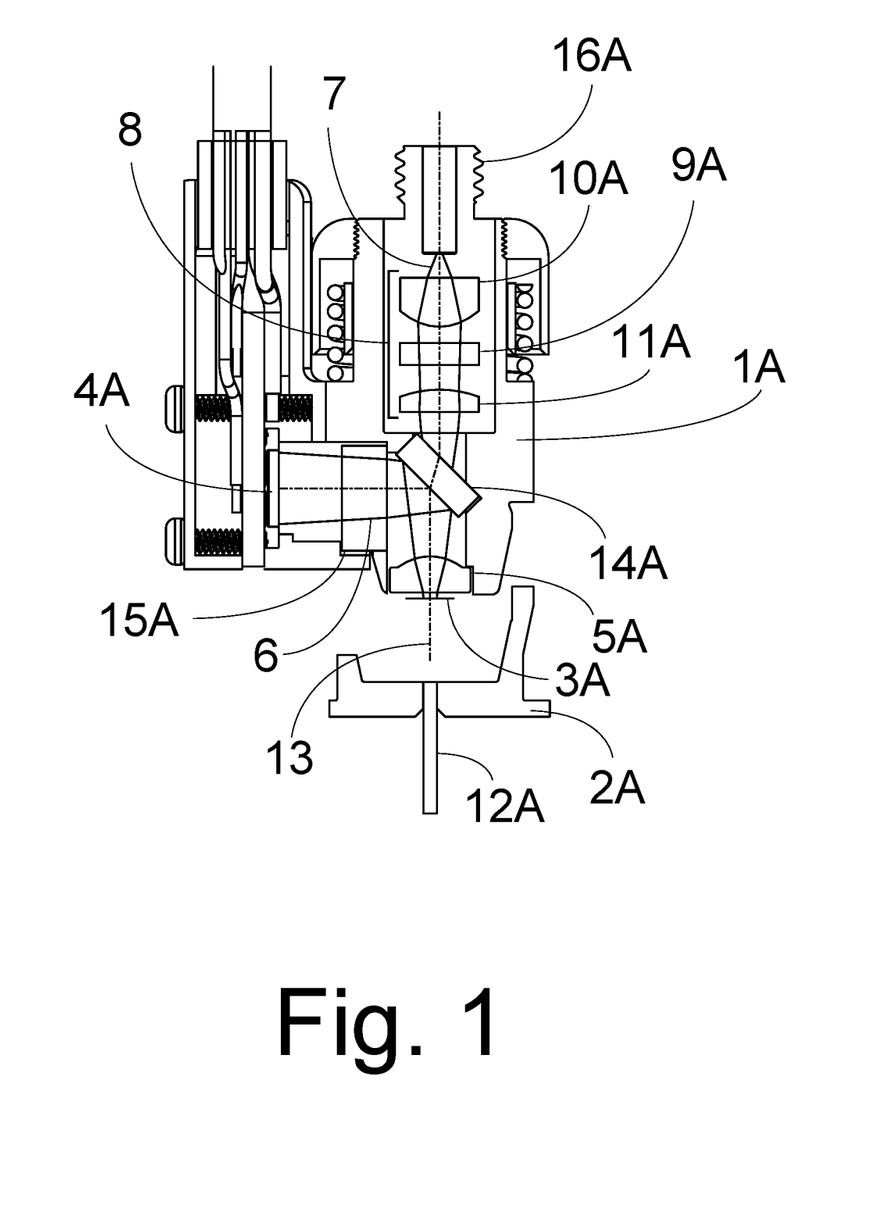
FIG. 1 is a side cross-section view and FIG. 2 is a front cross-section view of an exemplary miniaturized multimodal microscope system.
Figure 2:
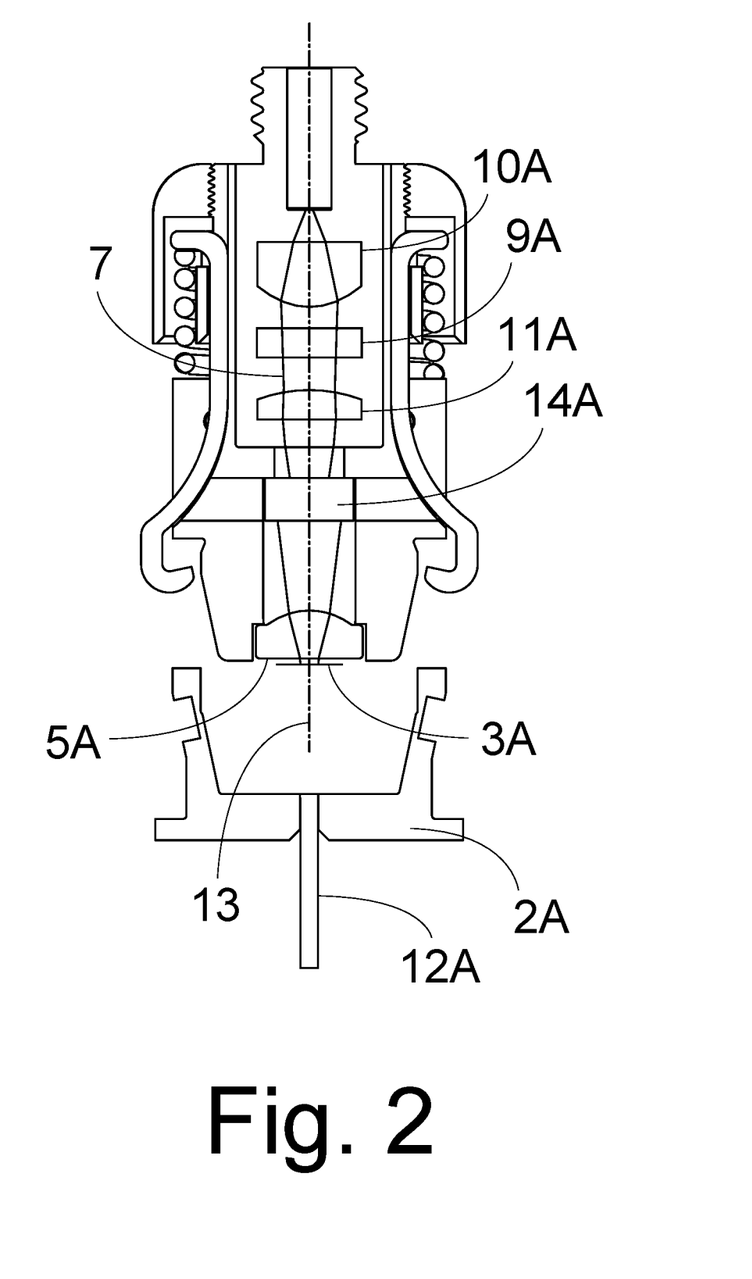

Referring now to FIG. 1 and FIG. 2, an example of a miniaturized microscope system for fluorescence measurement and optogenetic stimulation is shown in a side cross-section view and front cross-section view, respectively. A microscope body 1A has a connector adapted for connection to a cannula 2A that is attached to a sample, which is generally a biological test specimen for in vivo measurements as described in the above-incorporated U.S. patent application. The microscope, which includes microscope body 1A, also includes an optical interface 3A at the object plane of the optical system, an objective lens 5A, and a dichroic filter 14A to separate the returning image from the sample from the illumination pathway so that returning light from the sample is directed toward an image sensor 4A, such as a CMOS sensor array. The returning light is magnified by 2×-10× between the object plane at optical interface 3A and image sensor 4A. A gradient index (GRIN) relay lens 12A extends into the sample to image a region of interest and to optically excite fluorescent molecules and optically stimulate light-activated ion channels present in the sample in the region of interest. GRIN relay lens 12A is used to relay an image from deep structures in the sample to the object plane at optical interface 3A. GRIN relay lens 12A is integrated in cannula 2A and is optically aligned with an optical axis 13 of the objective lens 5A. GRIN relay lens 12A is not required for imaging surfaces just below cannula 2A. An illumination pathway 7 extends from a second connector 16A at the top of microscope body 1A that receives an optical coupling, such as an optical fiber, from at least two illumination sources that provide light of at least two nominal wavelengths, one for exciting fluorescence in the sample and the other for optogenetically stimulating the sample. An illumination lens system 8 including a high numerical aperture aspheric lens 10A and a plano-convex spherical lens 11A forms a collimated beam that is filtered by an excitation filter 9A which is then collimated at the optical interface 3A, i.e., at the object plane of the objective lens 5A, for introduction to GRIN relay lens 12A in cannula 2A along optical axis 13 after passing through dichroic filter 14A. A separate high numerical aperture aspheric lens 10A and plano-convex spherical lens 11A are not required, and a single high numerical aperture aspheric lens may be used instead, but using two lenses reduces the angle of incidence of light at the surface of excitation filter 9A and thereby improves filtering efficiency. Excitation filter 9A includes at least two optical transmission bands corresponding to the nominal wavelengths of the two illumination sources coupled through connector 16A, and cleans the illumination light before it is introduced to GRIN relay lens 12A, removing light artifacts such as auto-fluorescence generation in the optical fibers coupling the illumination light to second connector 16A. An emission filter 15A has a transmission band that admits light at the expected fluorescence wavelength of the sample, preventing light from the illumination sources entering image sensor 4A.

To reduce the number of optical components and thus the size of the microscope system, objective lens 5A may be a finite conjugate objective lens that generates a magnified image of the object plane at a fixed depth within the sample, so that no tube lens is required between objective lens 5A and image sensor 4A. To optimize aberration correction and increase the numerical aperture of the microscope, the exemplary microscope system features high numerical aperture aspheric objective lens 10A, which in the example has a numerical aperture between 0.3 and 0.5. To reduce the total size of the system, the focal length of objective lens 5A and any included tube lens are chosen to produce a magnification ratio below 10× between the object plane at optical interface 3A and image sensor 4A. In alternative embodiments, a tube lens is inserted in an imaging pathway 6 to adjust magnification and reduce angular divergence at the surface of emission filter 15A and thereby improve filtering efficiency. To avoid imaging artifacts due to illumination non-uniformity, the microscope system is configured to provide uniform illumination over the total field of view in the object plane at optical interface 3A. Illumination lens system 8 is configured to image the illumination at the back focal plane of objective lens 5A, which ensures that defects or dust present at the surface of the fiber optic that is connected to second connector 16A are not imaged in the object plane, which is especially important when illumination sources and microscope body 1A may be connected and disconnected many times.

Figure 3:
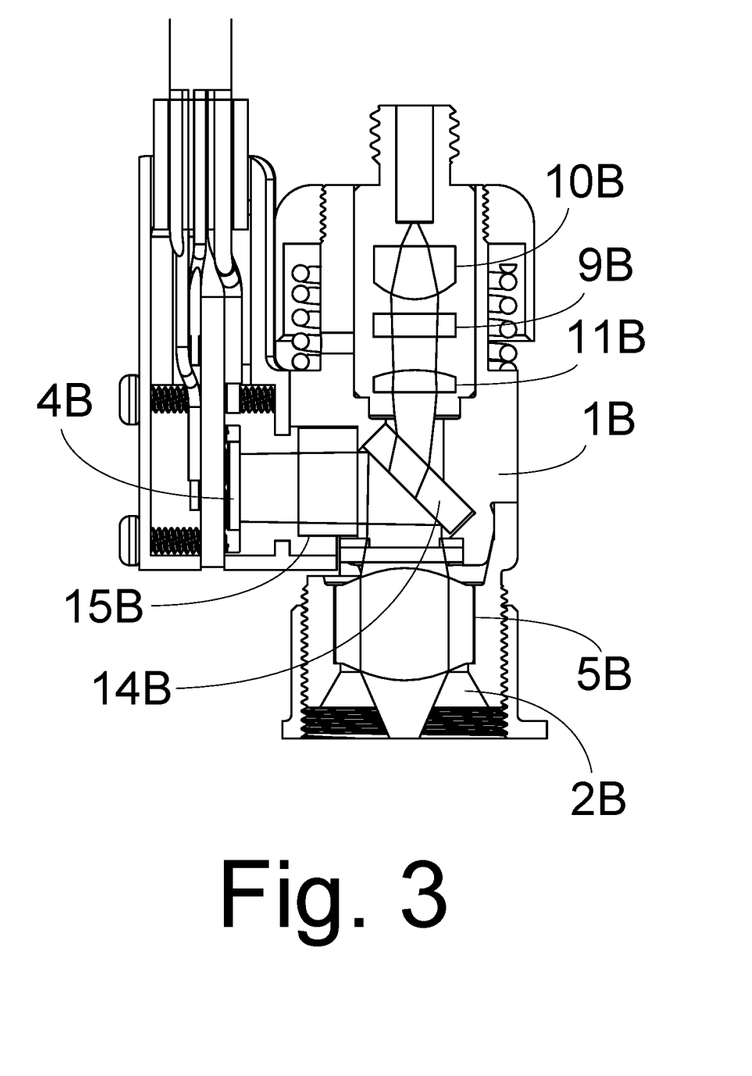
FIG. 3 is a side cross-section view of another exemplary miniaturized multimodal microscope system.

Referring now to FIG. 3, another example of a microscope system for fluorescence measurement and optogenetic stimulation is shown in a side cross-section view. The microscope system of FIG. 3 differs from the microscope system of FIGS. 1-2 in that the objective lens is integrated in a cannula 2B and is provided by a high numerical aperture objective lens 5B. Since the optical path differs from the microscope system of FIGS. 1-2, a high numerical aperture aspheric lens 10B, a plano-convex spherical lens 11B, an excitation filter 9B, an emission filter 15B and an image sensor 4B may be of different dimensions. A dichroic filter 14B and a microscope body 1B also generally have differing dimensions from dichroic filter 14A of FIGS. 1-2, but otherwise the remainder of the components integrated within microscope body 1B are similar or identical to and perform the same functions as the components in the microscope system of FIGS. 1-2. By including high numerical aperture objective lens 5B in cannula 2B, the working distance is increased up to 2.5 mm and the image field of view are increased up to 0.5 mm$^2$ without increasing invasiveness in the subject and no GRIN relay lens is required in the sample.

Figure 4:
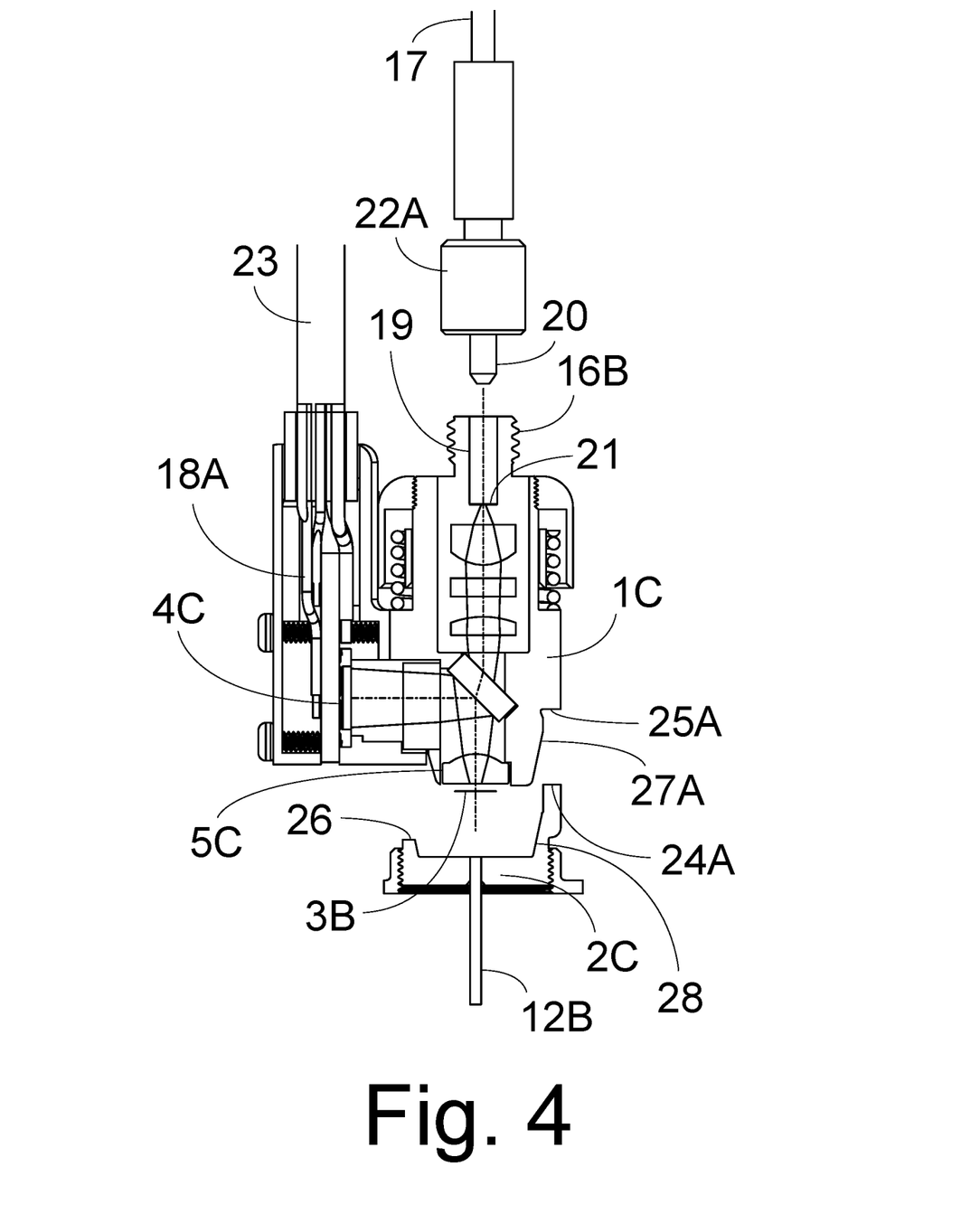
FIG. 4 is a side cross-section view and FIG. 5 is a front cross-section view of yet another exemplary miniaturized multimodal microscope system.
Figure 5:
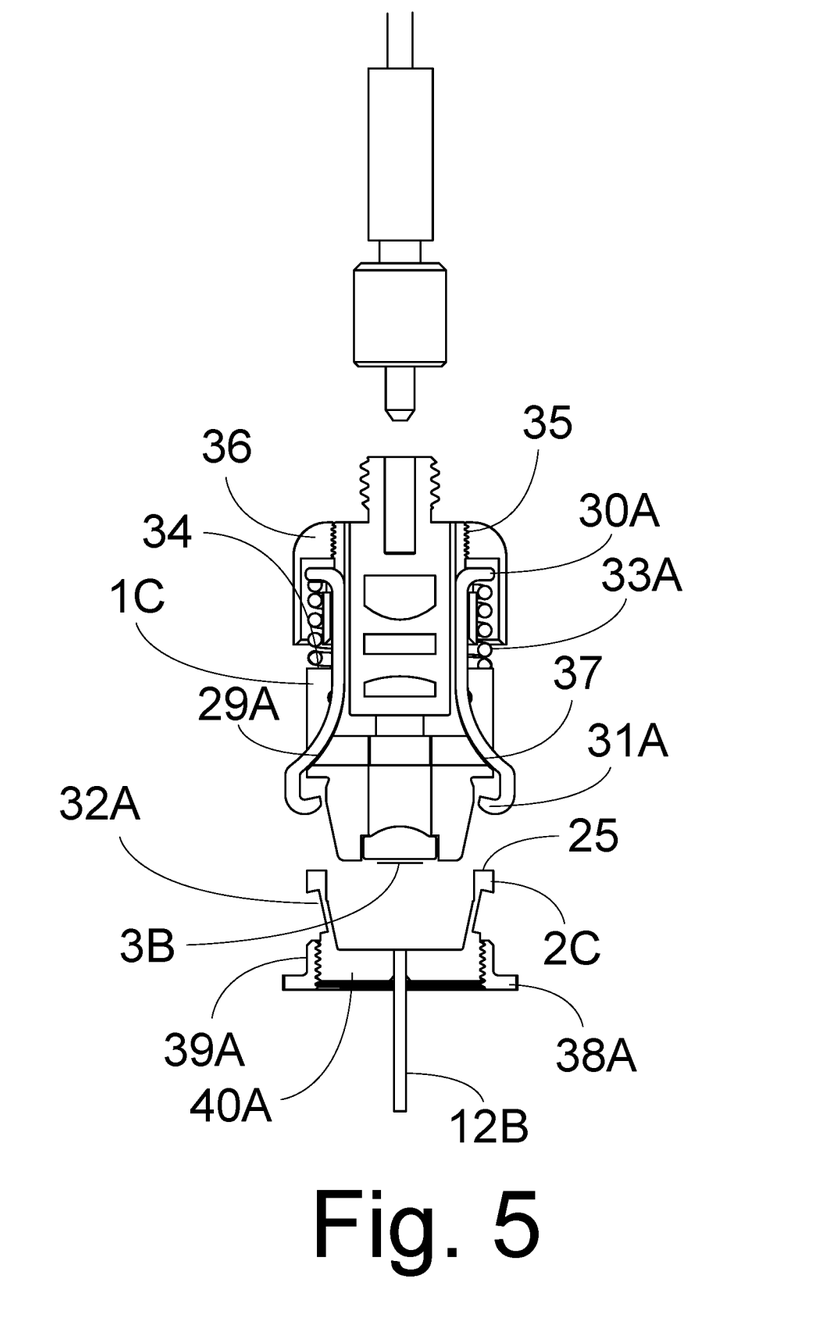

Referring now to FIG. 4 and FIG. 5, yet another example of a microscope system for fluorescence measurement and optogenetic stimulation is shown in a side cross-section view and front cross-section view, respectively. The microscope system of FIGS. 4-5 is similar to the microscope system of FIGS. 1-2, so only differences between them will be described in detail below. The microscope system of FIGS. 4-5 further includes an optical patch cord 17, e.g., multi-mode optical fiber or fiber bundle that conducts the light of two different illumination wavelengths from the two illumination sources such as those described above with reference to FIGS. 1-2. A threaded female connector 22A mates with a male threaded connector 16B of a microscope body 1C. A bored recess 19 in microscope body 1C receives a ferrule 20 that holds the terminated end of optical patch cord 17, which contacts a hub 21 providing an optical interface receiving the illumination light, i.e., the light for fluorescence excitation combined with the light for optogenetic stimulation, which is directed to an optical interface 3B at the object plane of an objective lens 5C for introduction to a GRIN relay lens 12B in a cannula 2C. An electrical cable 23 provides the electrical interface to an image sensor 4C which includes the control and data signals 18A needed to read image data from image sensor 4C, as well as power to operate image sensor 4C. While the illustrated system includes wired connections to image sensor 4C, in other examples the microscope system may be operated via wireless control using an integrated microcontroller and radio-frequency (RF) transceivers or optical transceivers. Further, the connections to the microscope systems may be made with rotary joints to prevent entanglement and alleviate stress that might otherwise be applied to the interface cables and fiber optics when used on freely moving specimens. A hybrid rotary joint incorporating electrical and fiber optic connections can be provided for this purpose.

Cannula 2C, includes an orientation key 26, which provides rotational alignment of cannula 2C with microscope body 1C. An interior top surface 28 of cannula 2C is shaped to adapt cannula 2C to accept a guiding taper 27A around the bottom portion of microscope body 1C and a cylindrical shoulder 24A contacts a corresponding shoulder 25A on microscope body 1C to prevent movement of microscope body 1C with respect to cannula 2C once microscope body 1C is secured to cannula 2C. A precise optical alignment between objective lens 5C and GRIN relay lens 12B is achieved once microscope body 1C is secured to cannula 2C. As seen in FIG. 5, additional components that secure microscope body 1C to cannula 2C are shown. A latch hook 31A expands to latch around a shoulder 25 that defines a slot 32A around the exterior surface of cannula 2C and the inner surface of an extension 29A of latch hook 31A slides along side walls 37 of microscope body 1C. Side walls 37 of microscope body 1C are shaped to form an acute angle with respect to the cylindrical axis of the cannula 2C, so that, when latch hooks 31A are moved downwards toward cannula 2C, side walls 37 act as guides for expanding latch hooks 31A to release shoulder 25 of cannula 2C. The upper end of latch hook 31A forms a retention shoulder 30A secured by a locking nut 36 threaded onto a male threaded portion 35 of microscope body 1C, and which compresses a compression spring 33A that provides for secure latching of latch hooks 31A by pressing against the lower surface of retention shoulder 30A and a shoulder 34 on microscope body 1C to pull latch hooks 31A upwards. Cannula 2C and microscope body 1C are connected by pressing on latch hooks 31A toward cannula 2C. Tightening locking nut 36 on microscope body 1C before pressing on latch hooks 31A, reduces the force applied on the subject. A pin may be inserted between latch hooks 31A and cannula 2C to release latch hooks 31A from slot 32A. Cannula 2C is secured to the specimen being observed, in general, by fastening a flange 38A of cannula 2C to the specimen with an adhesive or with fasteners such as screws. The flange 38A is attached to a body 40A of cannula 2C. To adjust the focus and the working distance of the microscope system, cannula 2C includes a focus adjustment ring 39A that is glued and/or screwed on the specimen via flange 38A. In the example, body 40A of the cannula 2C includes a male threaded portion on an outer surface. A threaded female inner surface of focus adjustment ring 39A mates with a threaded male portion of body 40A and is rotated to adjust the distance between the microscope system and the specimen when focus adjustment ring 39A is attached to the specimen.

Figure 6:
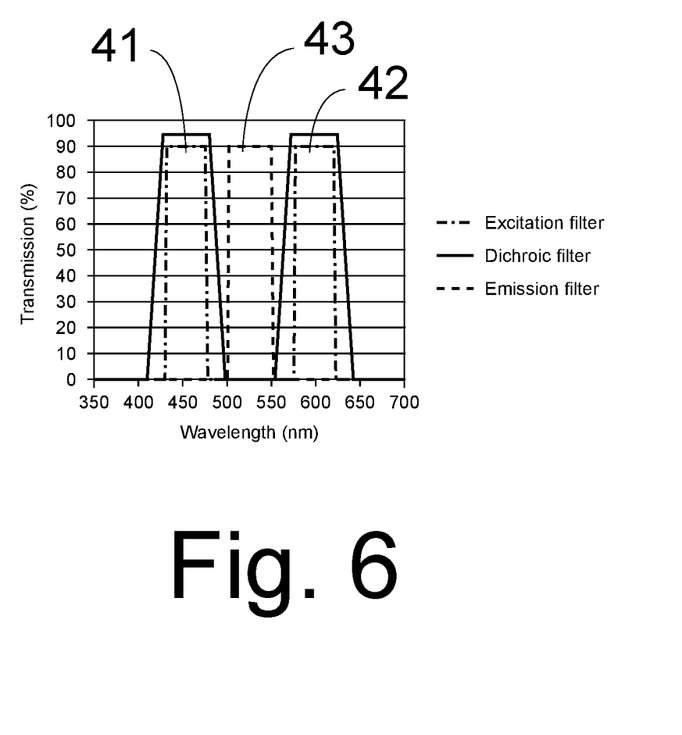
FIG. 6 is a graph depicting optical transmission band characteristics of filters that may be used within the miniaturized multimodal microscope systems depicted herein.

FIG. 6 illustrates the optical band-pass characteristics of filter components in the above-described microscope systems. Excitation filter 9 includes transmission bands for two illumination bands/wavelengths 41 and 42, which in the example correspond to the wavelength for optogenetic stimulation and fluorescent excitation, respectively. Another transmission band for an emission band/wavelength 43 corresponds to the emission spectrum of the fluorescent sample, and illustrates a suitable band-pass characteristic for emission filters 15A, 15B as described above. Further, if the fluorescence emission band/wavelength 43 is between the two illumination bands/wavelengths 41, 42, then the band-pass characteristic of dichroic filters 14A, 14B in the through direction can be similar (or identical) to the dual transmission band characteristic of excitation filters 9A, 9B. Otherwise if the emission band/wavelength 43 is of longer wavelength(s) than the two illumination bands/wavelengths 41, 42, then a short-pass characteristic can be used for dichroic filters 14A, 14B in the through direction.

Figure 7:
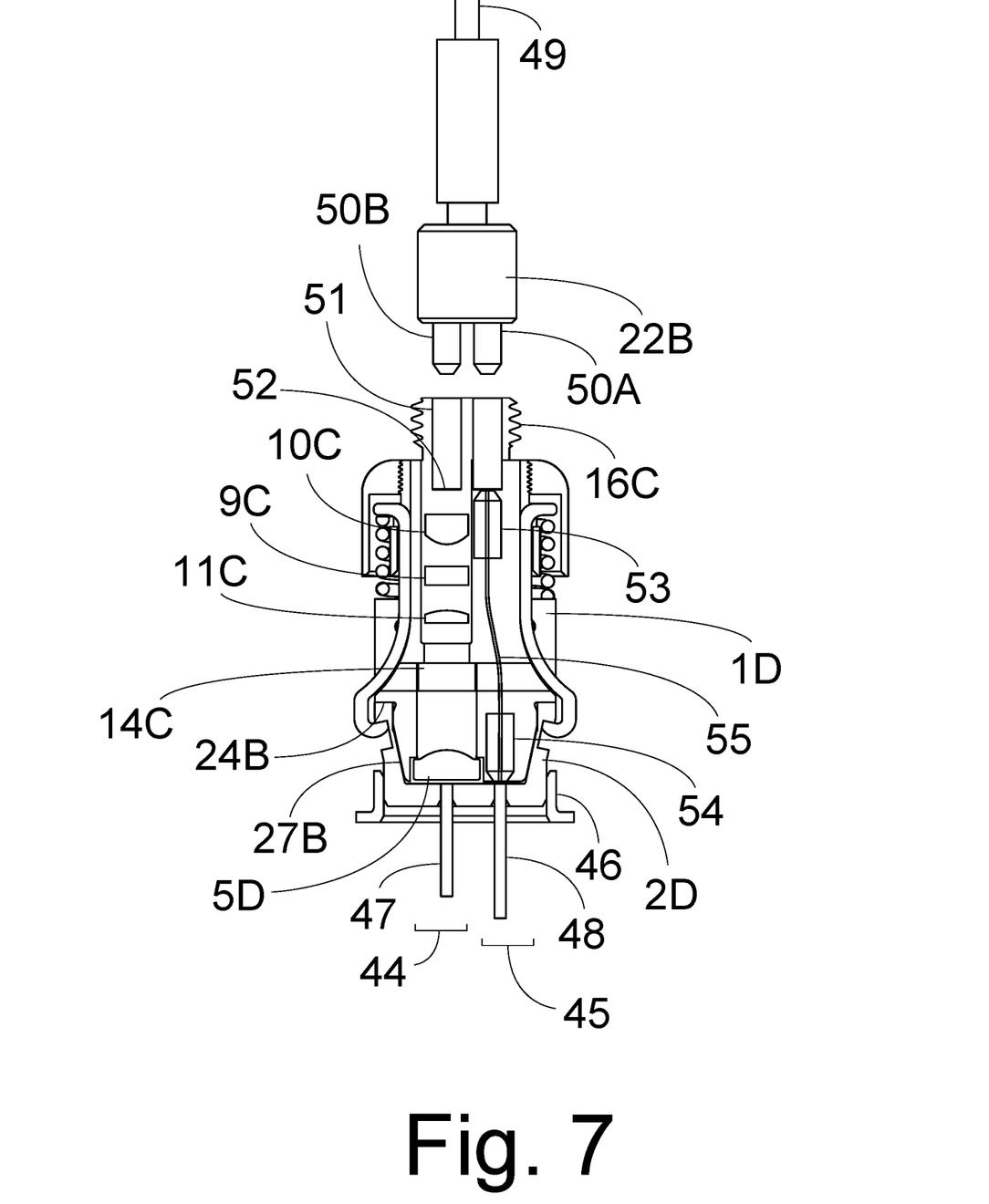
FIG. 7 is a front cross-section view of still another exemplary miniaturized multimodal microscope system.

Referring now to FIG. 7, still another example of a microscope system for fluorescence measurement and optogenetic stimulation is shown in a front cross-section view. The microscope system of FIG. 7 differs from the microscope system of FIGS. 1-5 in a cannula 2D includes two optical probes, one of which is a fiber optic implant 48 for optogenetic stimulation and one a GRIN lens 47 for fluorescence imaging. Cannula 2D is affixed to the subject with a mounting ring 46. Since the optical paths differ from those in the microscope systems of FIGS. 1-5, a high numerical aperture aspheric lens 10C, a plano-convex spherical lens 11C, and an excitation filter 9C will generally be of different dimensions from their corresponding components in microscope systems of FIGS. 1-5. A dichroic filter 14C and a microscope body 1D also generally have differing dimensions, but otherwise the remainder of the components integrated within microscope body 1D are similar or identical to and perform the same functions as the components in the microscope systems of FIGS. 1-5. The fluorescence imaging portion of the microscope system of FIG. 7 images a first region 44 within the sample along a fluorescence imaging optical pathway, while the optogenetic stimulation portion stimulates the sample in a second region 45 along an optogenetic stimulation pathway. A dual fiber optical patch cord 49 includes separate fibers/bundles for the optogenetic illumination and fluorescence illumination. Fiber optic patch cord 49 is secured to microscope body 1D by a threaded cap 22B that is threaded onto a male threaded connector 16C of microscope body 1D. The optogenetic illumination is provided from a fiber terminating at the end of a first ferrule 50A, which couples the optogenetic stimulation light to a guiding ferrule 53 of an internal optical fiber 55 that conducts light to another guiding ferrule 54 securing a termination end of internal optical fiber 55 to provide the optical interface that abuts a top end of fiber optic optogenetic stimulation implant 48 when microscope body 1D is secured to cannula 2D. Microscope body 1D is secured to cannula 2D using a releasable latch hook arrangement as described above with reference to FIGS. 4-5 that pulls cannula 2D against a shoulder 24B on microscope body 1D. An interior surface 27B of cannula 2D is shaped to mate with the exterior lower surface of microscope body 1D. For the fluorescence imaging channel, another fiber from dual fiber optical patch cord 49 is inserted in a channel 51 in microscope body 1D. Optical fiber patch cord 49 terminates at the end of a second ferrule 50B and couples the fluorescence excitation stimulation light to a hub 52 that conducts light through a lens system as illustrated in FIGS. 1-5 to provide the fluorescence excitation illumination to and receiving fluorescence emissions from an objective lens 5D. Objective lens 5D couples the fluorescence excitation and emissions to and from GRIN lens 47, which couples the excitation to the sample and receives the emissions from the sample.

Figure 8:
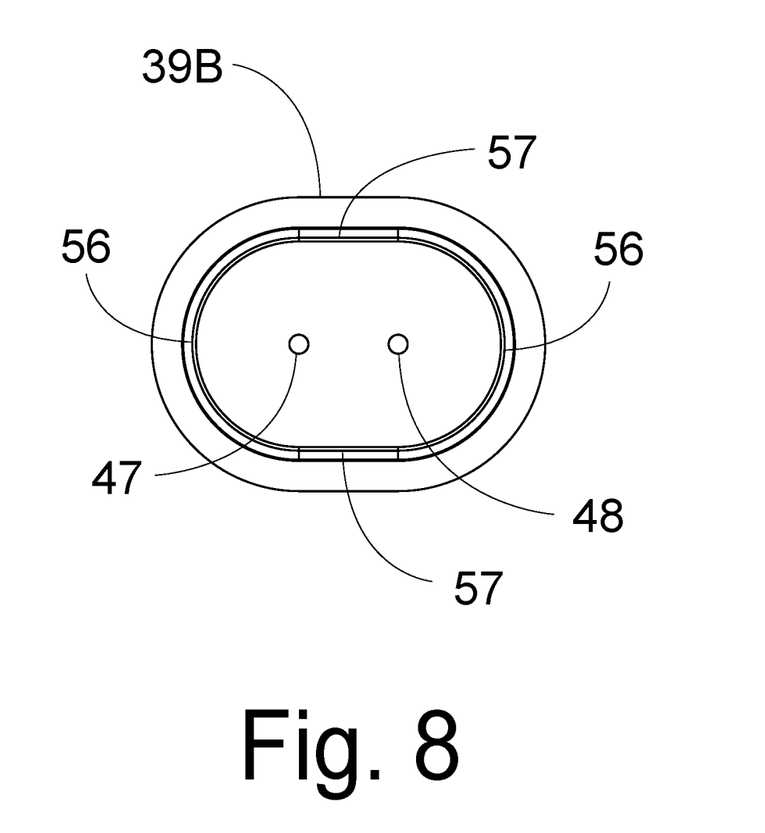
FIG. 8 is a top view and FIG. 9 is a side cross-section view of an exemplary cannula for use in the exemplary miniaturized multimodal microscope systems of FIG. 7 and FIGS. 10-12.
Figure 9:
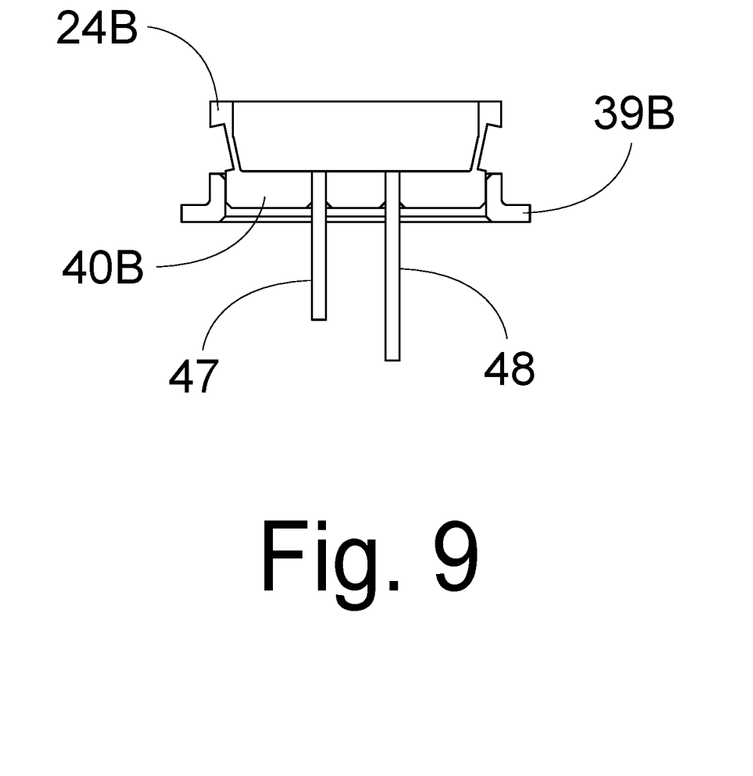

Referring now to FIG. 8 and FIG. 9, details of cannula 2D are shown in a top view and a side cross-section view, respectively. A shoulder 24B around the top of cannula 2D and the internal mating wall surfaces have a shape that is semi-cylindrical at each end 56 and a flattened portion 57 formed in the middle of the outline to accommodate both the optogenetic stimulation implant 48 and GRIN lens 47. A body 40B of cannula 2D attaches to the specimen via a focus adjustment ring 39B that has flattened extensions for adhering to the specimen. Focus adjustment ring 39B slides along the body 40B of cannula 2D to adjust the focus of the microscope system.

Figure 10:
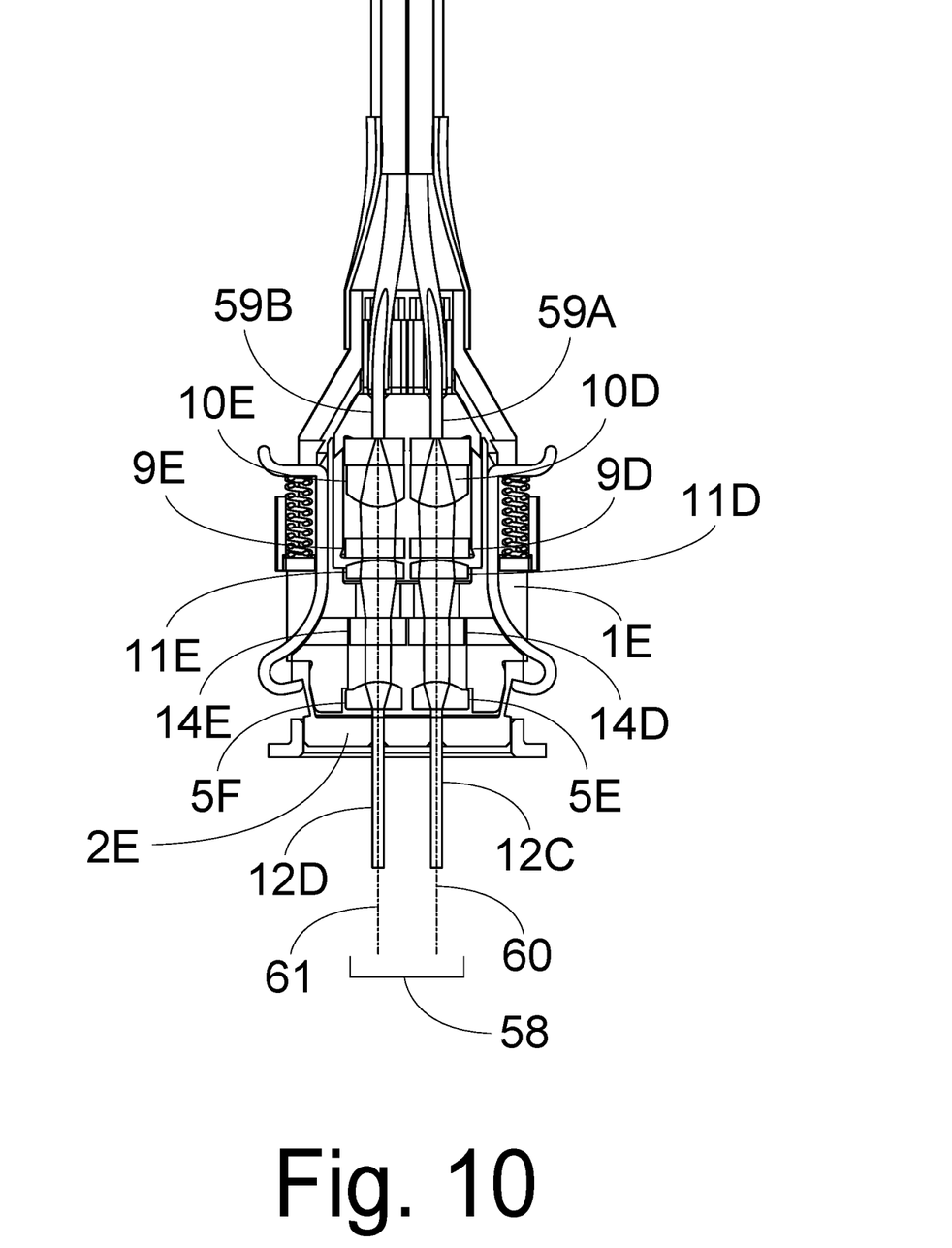
FIG. 10 and FIG. 12 are front cross-section views and FIG. 11 is a side cross-section view of another exemplary miniaturized multimodal microscope system.
Figure 11:
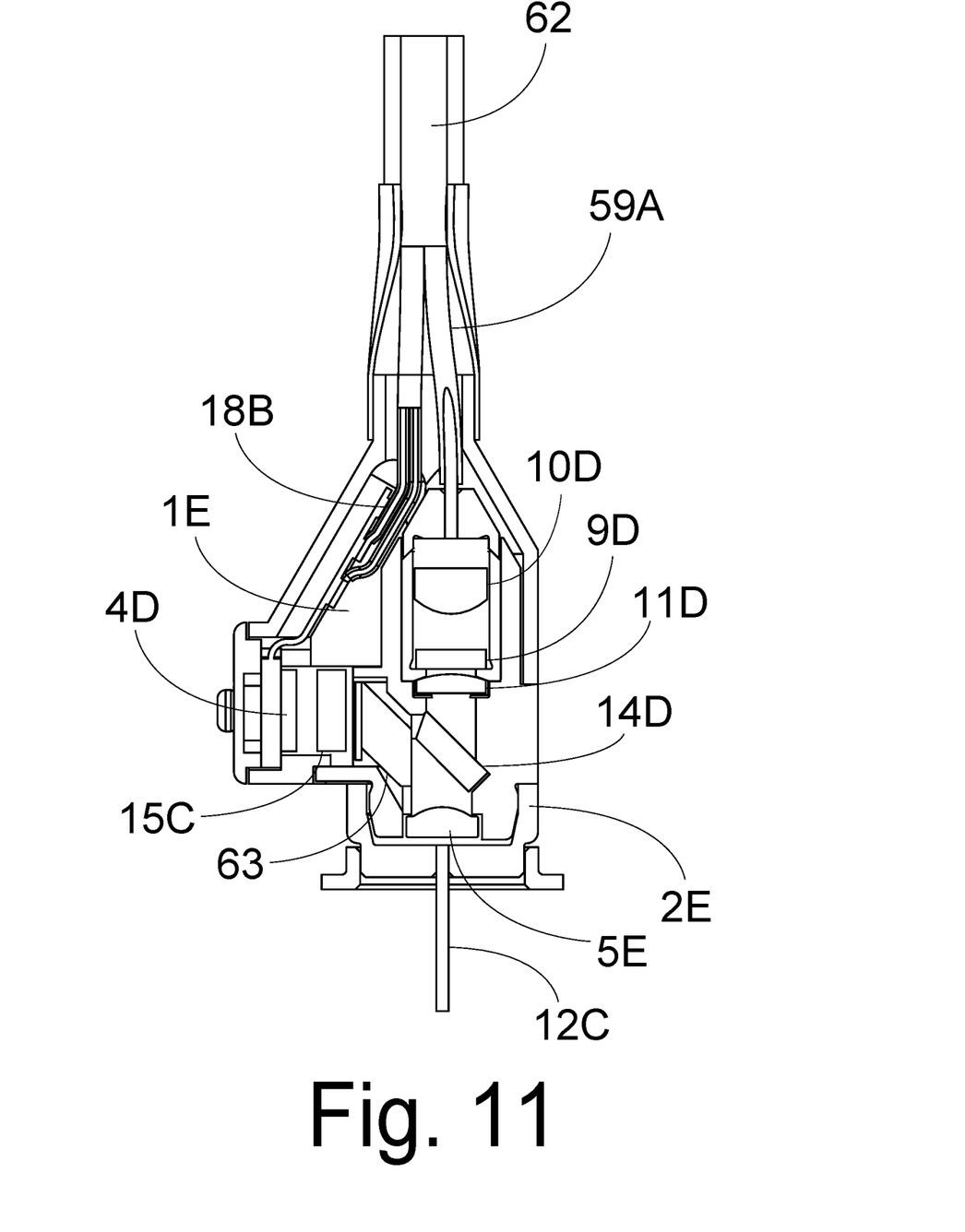
Figure 12:
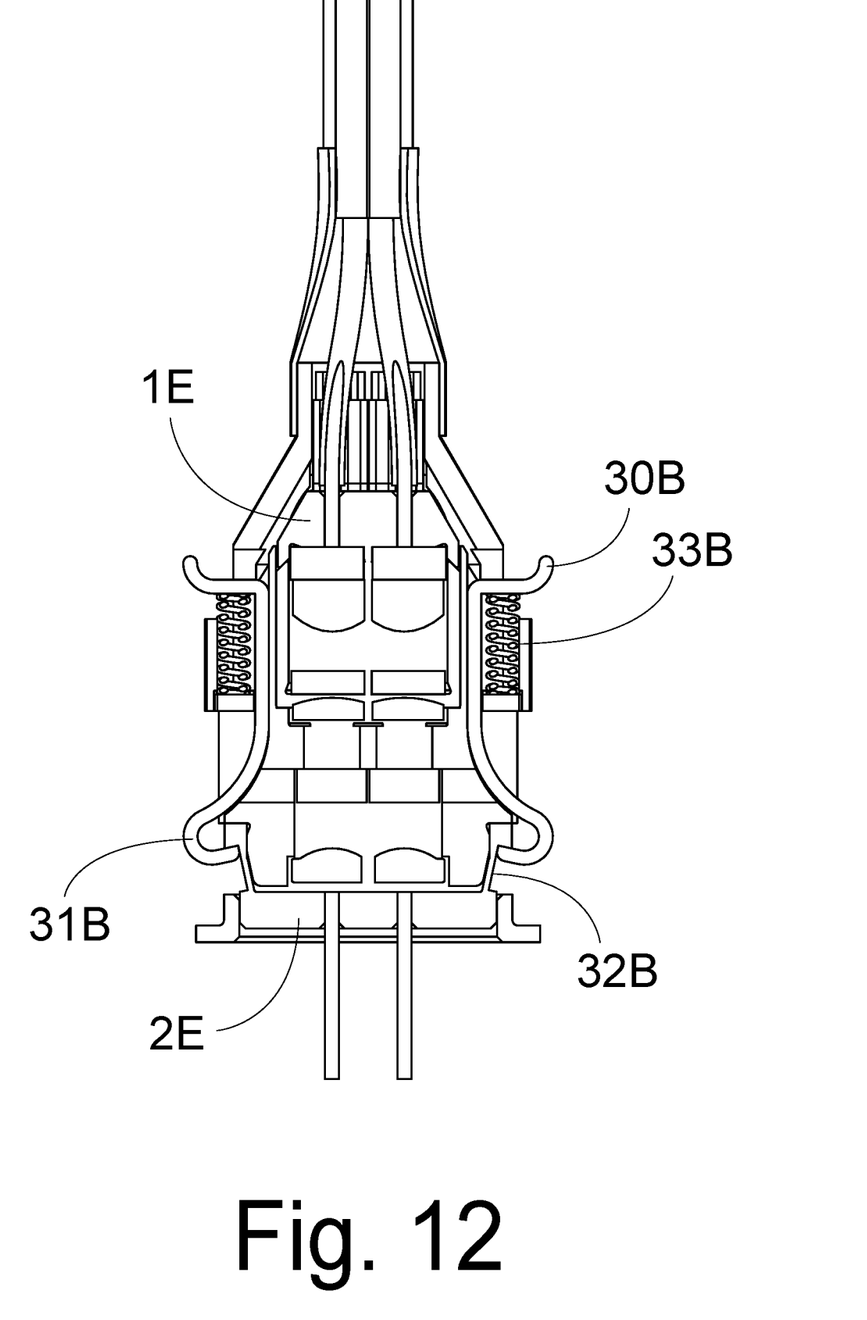

Referring now to FIGS. 10-12, another example of a miniaturized microscope system for fluorescence measurement and optogenetic stimulation is shown. FIG. 11 is a side cross-section view and FIG. 10 and FIG. 12 are front cross-section views of the microscope system. The illustrated microscope system can support up to four channels of measurement, two fluorescence imaging channels and two optogenetic stimulation channels by including a cannula having two relay lenses 12C, 12D such as GRIN lenses that can be used to illuminate regions at the ends of relay lenses 12C, 12D in the sample at two different wavelengths each, one for optogenetic stimulation and one for fluorescence excitation. Alternatively the microscope system can be used to provide two independent fluorescence imaging channels without optogenetic stimulation. Returning light from regions 58 at the bottom ends of relay lenses 12C, 12D and guided to the top ends of relay lenses 12C, 12D is captured by a pair of high numerical aperture aspheric objective lenses 5E, 5F within a microscope body 1E and is directed by a pair of dichroic filters 14D, 14E through a pair of rhomboid prisms 63 and a pair of emission filters 15C to a pair of image sensors 4D. Rhomboid prisms 63 are provided to allow independent optical pathways 60 and 61 to be imaged onto image sensors 4D separated by a fixed distance and the distance between the images can be controlled by rotating rhomboid prisms 63. Alternatively, image sensor 4D may be a single image sensor configured to capture both fields of view from both objective lenses 5E, 5F. The illumination light (both the fluorescence excitation wavelength and the optogenetic stimulation wavelength for each channel) is provided by a pair of optical fibers 59A, 59B included in a connection cable 62, which also includes electrical cables 18B for interfacing to and powering image sensors 4D. Each channel includes an excitation filter 9D, 9E, which may have identical characteristics if the optogenetic stimulation and fluorescence excitation wavelengths are the same for both channels, or the two excitation filters 9D, 9E may differ. Both excitation filters 9D, 9E will generally have the dual band-pass type of characteristic described above with reference to FIG. 6 and filter the illumination provided through optical fibers 59A, 59B and through a pair of high numerical aperture collimation aspheric lenses 10D, 10E. (If the system is used for fluorescence imaging only, then the excitation filters 9D, 9E require only a single transmission band.) The pair of emission filters 15C will also generally have characteristics as described above with reference to FIGS. 1-2. A pair of plano-convex spherical lenses 11D, 11E directs the illumination light received from excitation filters 9D, 9E and focuses the light at the back focal planes of high numerical aperture aspheric objective lenses 5E, 5F, which provide a pair of optical interfaces at the top terminations of relay lenses 12C, 12D when microscope body 1E is coupled to a cannula 2E.

Cannula 2E has an interior top surface shaped to adapt cannula 2E to accept the guiding taper around the bottom portion of microscope body 1E. Additional components that secure microscope body 1E to cannula 2E are shown. A shoulder on cannula 2E contacts a corresponding shoulder on microscope body 1E to prevent movement of microscope body 1E with respect to cannula 2E once microscope body 1E is secured to cannula 2E. A precise optical alignment between the objective lenses 5E, 5F and their corresponding relay lenses 12C, 12D is obtained once microscope body 1E is secured to cannula 2E. A latch hook 31B expands to latch around a slot 32B formed around the exterior surface of cannula 2E and the inner surface of latch hook 31B slides along a side wall of microscope body 1E. The upper end of latch hook 31B forms a retention shoulder 30B that is loaded by a compression spring 33B that provides for secure latching of latch hook 31B by pressing against the lower surface of retention shoulder 30B to pull latch hook 31B upwards. Pulling latch hook 31B upwards also provides a secure three-dimensional alignment of cannula 2E with microscope body 1E. A pin may be inserted between latch hook 31B and cannula 2E to release latch hook 31B from slot 32B.

While the invention has been particularly shown and described with reference to the preferred embodiment thereof, it will be understood by those skilled in the art that the foregoing and other changes in form, and details may be made therein without departing from the spirit and scope of the invention.

What is claimed:

1. A miniature microscope for performing simultaneous or sequential optogenetic stimulation and fluorescence measurements on a sample having an attached optical cannula, the microscope comprising:
    a microscope body having a first connector for receiving at least one first optical illumination connection coupling light from at least two illumination sources having differing illumination wavelengths;
    a second connector of the microscope body adapted to mechanically connect to the cannula and optically align the cannula with the microscope body and having at least one optical interface for coupling light returning from the sample to the microscope and illumination from the at least two illumination sources to the sample; and
    a first optical filter having a dual band-pass characteristic for filtering the light coupled from the at least two illumination sources, wherein a first transmission band of the first optical filter passes light having a first wavelength corresponding to a first one of the illumination sources and the second transmission band of the first optical filter passes light having a differing second wavelength corresponding to a second one of the illumination sources.

2. The microscope of claim 1, further comprising an objective lens providing or coupled to the at least one optical interface of the second connector.

3. The microscope of claim 2, further comprising:
    an image sensor for receiving an image from the objective lens;
    a second optical filter having a dichroic characteristic optically coupled between the objective lens and the image sensor, whereby light coupled from the at least two illumination sources is directed to the at least one second optical connection, and whereby the light returning from the sample through the objective lens is directed to the image sensor.

4. The microscope of claim 1, wherein the first wavelength of the first illumination source is a wavelength for optogenetic stimulation of the sample, and wherein the second wavelength of the second illumination source is a wavelength for fluorescence imaging of the sample.

5. The microscope of claim 1, wherein the at least two illumination sources comprises a first illumination source and a second illumination source, and wherein the at least one optical interface comprises a first optical interface for coupling light returning from a first region within the sample to the microscope and coupling light from the first illumination source to the first region within the sample, and a second optical interface for coupling light from the second illumination source to a second region of the sample that is different from the first region.

6. The microscope of claim 5, wherein the first region and the second region are spacially separated areas within the sample.

7. The microscope of claim 5, wherein the second optical interface further couples light returning from the second region of the sample.

8. The microscope of claim 7, wherein the first optical filter filters the light coupled from the first illumination source to the first optical interface and further comprising a second optical filter having a dual band-pass characteristic for filtering the light coupled from the second illumination source to the second optical interface.

9. A miniature microscope for performing simultaneous or sequential optogenetic stimulation and fluorescence measurements on a sample having an attached optical cannula, the microscope comprising:
    a first connector for receiving at least one first optical illumination connection coupling light from at least one illumination source; and
    a second connector adapted to mechanically connect to the cannula and having a first optical interface for coupling light returning from a first region within the sample to the microscope and coupling light from the at least one illumination source to the first region within the sample, and a second optical interface for coupling light from the at least one illumination source to a second region of the sample that is different from the first region.

10. The microscope of claim 9, wherein the first region and the second region are spacially separated areas within the sample.

11. The microscope of claim 9, wherein the second optical interface couples light returning from the second region within the sample to the microscope.

12. A method of performing simultaneous or sequential optogenetic stimulation and fluorescence measurements on a sample having an attached optical cannula, the method comprising:
    receiving at least one first optical illumination connection coupling light from at least two illumination sources having differing illumination wavelengths at a microscope;
    mechanically connecting to the cannula with a first connector having at least one optical interface for coupling light returning from the sample to the microscope and illumination from the at least two illumination sources to the sample;
    filtering the light coupled from the at least two illumination sources with a first optical filter having a dual band-pass characteristic, wherein a first transmission band of the first optical filter passes light having a first wavelength corresponding to a first one of the illumination sources and the second transmission band of the first optical filter passes light having a differing second wavelength corresponding to a second one of the illumination sources.

13. The method of claim 12, receiving the light returning from the sample with an objective lens integrated within the microscope.

14. The method of claim 12, further comprising:
    receiving an image from the objective lens with an image sensor integrated within the microscope; and
    separating light coupled from the at least two illumination sources that is coupled from the at least one first optical connection from light returning from the sample through the objective lens that is directed to the image sensor with a second optical filter having a dichroic characteristic optically coupled between the objective lens and the image sensor.

15. The method of claim 12, wherein the first wavelength of the first illumination source is a wavelength for optogenetic stimulation of the sample, and wherein the second wavelength of the second illumination source is a wavelength for fluorescence imaging of the sample.

16. The method of claim 12, wherein the at least two illumination sources comprises a first illumination source and a second illumination source, and wherein the first connector has a first optical interface for coupling light returning from a first region within the sample to the microscope and coupling light from the first illumination source to the first region within the sample, and a second optical interface for coupling light from the second illumination source to a second region of the sample that is different from the first region.

17. The method of claim 16, wherein the first region and the second region are spatially separated areas within the sample.

18. The method of claim 17, wherein the second optical interface further couples light returning from the second region of the sample.

19. The method of claim 18, wherein the first filtering filters the light coupled from the first illumination source to the first optical interface, and wherein the method further comprises second filtering the light coupled from the second illumination source to the second optical interface with a second optical filter having a dual band-pass characteristic.

20. A method of performing simultaneous or sequential optogenetic stimulation and fluorescence measurements on a sample having an attached optical cannula, the method comprising:

receiving at least one first optical illumination connection coupling light from at least one illumination source at a microscope through a first connector;

mechanically connecting to the cannula with a second connector coupling illumination from the at least one illumination source to the sample having a first optical interface for coupling light returning from a first region within the sample to the microscope and coupling light from the at least one illumination source to the first region within the sample, and a second optical interface for coupling light from the at least one illumination source to a second region of the sample that is different from the first region.

21. The method of claim 20, wherein the second optical interface further couples light returning from the second region of the sample.

\* \* \* \* \*